US006436903B1

(12) United States Patent
Clayberger et al.

(10) Patent No.: US 6,436,903 B1
(45) Date of Patent: *Aug. 20, 2002

(54) IMMUNOMODULATING COMPOUNDS COMPRISING D-ISOMERS OF AMINO ACIDS

(75) Inventors: Carol A. Clayberger; Alan M. Krensky, both of Stanford, CA (US)

(73) Assignee: Stanford University (Board of Trustees of the Leland Standford Junior University), Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/651,650

(22) Filed: May 22, 1996

(51) Int. Cl.$^7$ ................................................ A61K 38/00
(52) U.S. Cl. ........................................ 514/15; 530/328
(58) Field of Search ............................... 514/2, 12, 13, 514/14, 15; 530/300, 324, 325, 326, 327, 328

(56) References Cited

U.S. PATENT DOCUMENTS 5,171,838 A * 12/1992 Chiba et al. ................ 530/326
5,589,458 A * 12/1996 Jameson et al. ............ 514/13

FOREIGN PATENT DOCUMENTS

| WO | WO 88/05784 | 8/1988 |
| WO | WO 90/10016 | 9/1990 |
| WO | WO 93/17699 | 9/1993 |

OTHER PUBLICATIONS

Karin et al., J. Exp. Med. vol. 180, 2227–2237, 1994, Dec. 1994.*
Nisco et al. J. Immunology, vol. 152:3786–3792, Feb. 1994.*
Buelow et al., Transplantation, vol. 59:455–460, Feb. 1995*
S. Nisco et al., "Induction of Allograft Tolerance in Rats by an HLA Class–1–Derived Peptide and Cyclosporine A[1]," Journal of Immunology (1994) 152:3786–3792.
M.C. Cuturi et al., "Prolongation of Allogeneic Heart Graft Survival in Rats by Administration of a Peptide (a.a. 75–84) from the α1 Helix of the First Domain of HLA–B7 01," Transplantation (1995) 59:661–669.
Auffray et al., J. Human Immunology (1986) 15:381–390.
Biddison,.et al., J. Immunol. (1980) 124:548–552.
Clayberger, et al., J. Exp. Med. (1985) 11:1709–1714.
Cowan, et al., J. Immunol. (1985) 135:2835–2841.
Duran, et al., Transplantation (1986) 41:279–285.
Gaston, et al., J. Exp. Med. (1983) 158:280–293.
Holmes, et al., EMBO J. (1985) 4:2849–2854.
Koller, et al., J. Immunol. (1985) 134:2727–2733.
Krangel, Biochemistry (1982) 21:6313–6321.
Krangel, et al., J. Immunol. (1983) 130:1856–1862.
Nathenson, et al., Ann. Rev. Immunol. (1986) 4:471–502.
Pierschbacher, et al., Nature (1984) 309:30–33.
Salter, et al., J. Exp. Med. (1987) 166:283–288.
Schulz, et al., Proc. Natl. Acad. Sci. USA (1983) 80:2007–2011.
Spits, et al., Immunogenetics (1982) 16:503–512.
Taketani, et al., J.Immunol. (1984) 133:816–821.
Townsend, et al., Cell (1986) 44:959–968.
Vega, et al., Proc. Natl. Acad. Sci. USA (1985) 82:7394–7398.
Ways, et al., J. Biol. Chem. (1985) 26:11924–11933.
Yamada, et al., J. Cell Biol. (1985) 28:99–104.
Buelow et al., "Immunomodulation by Soluble HLA Class I," Transplantation Mar. 15, 1995, vol. 59, No. 5, pp. 649–654.

* cited by examiner

Primary Examiner—Patrick J. Nolan
(74) Attorney, Agent, or Firm—Morrison & Foerster LLP

(57) ABSTRACT

Compounds having immunomodulatory activity which are peptide-type compounds, or variants or fragments thereof, including the N-terminal acylated and C-terminal amidated or esterified forms of up to 30 amino acids wherein the peptide-type compound comprises the formula:

(a) R $aa^{76-77}$ L $aa^{79-84}$ or
(b) $aa^{84-79}$ L $aa^{77-76}$ R wherein:
$aa^{76}$ is E or V;
$aa^{77}$ is D, S or N;
$aa^{79}$ is R or G;
$aa^{80}$ is I or N;
$aa^{81}$ is a small or hydrophobic amino acid
$aa^{82}$ is R or L;
$aa^{83}$ is G or R;
$aa^{84}$ is a small or hydrophobic amino acid;
wherein, in said compounds,
at least one of the amino acids is the D isomer
are used by themselves or in combination with immunosuppressant drugs, to reduce CTL activation, particularly in association with transplantation.

3 Claims, No Drawings

IMMUNOMODULATING COMPOUNDS COMPRISING D-ISOMERS OF AMINO ACIDS

TECHNICAL FIELD

The field of this invention is immunomodulation.

BACKGROUND

The immune system plays a crucial role in the defense of mammalian hosts against pathogenic organisms and aberrant indigenous cells, such as in neoplasia. Included in the defense mechanism are cytotoxic T-lymphocytes ("CTL") which serve to monitor the infection of cells by pathogenic organisms and the presence of neoplastic cells. They also attack cells having a different major histocompatibility complex repertoire from the host. Under certain conditions, the CTL attack indigenous cells, resulting in a group of diseases referred to as autoimmune diseases.

For transplantation and autoimmune diseases one would wish to be able to inhibit the CTLs from attacking the tissue. For the most part, today, in order to inhibit CTLs, immunosuppressants are employed, which generally debilitate the immune system. As a result, the patient is much more susceptible to adventitious infection, as well as numerous side effects resulting from the drugs, such as cyclosporin A and FK506. There is, therefore, substantial interest in providing alternative methods for inhibiting immune attack in the cases of transplantation and in autoimmune diseases, where the inhibition is more specific, has fewer side effects, and may be longer lasting.

Relevant Literature

Clayberger, et al., *J. Exp. Med.* (1985) 11:1709–1714 describe HLA-A2 antigen in comparisons with HLA-Aw68 and Aw69. Townsend, et al., *Cell*, (1986) 44:959–968 suggests that CTL recognize segmental epitopes of denatured or degraded proteins in a similar way as helper T-cells. Holmes and Parham, *EMBO J.*, (1985) 4:2849–2854 describe the relationship of HLA-A2, Aw68 and Aw69. CTL target specificity has been taught to be extremely sensitive to changes in structure of human Class I molecules (Durna and Pease, *Transplantation*, (1986) 41:279–285: Biddison, et al., *J. Immunol.*, (1980) 124:548–552: Spits, et al., *Immunogenetics*, (1982) 16:503–512: Gaston, et al., *J. Exp. Med.* (1983) 158:280–293).

Mutants which affect recognition by CTL have been studied in mice (Nathenson, et al., *Ann. Rev. Immunol.* (1986) 4:471–502: Schulz, et al., *Proc. natl. Acad. Sci. USA* (1983) 80:2007–2011) and humans, (Krangel, *Biochemistry* (1982) 21:6313–6321: Krangel, et al., *J. Immunol.* (1983) 130:1856–1862: Cowan, et al., *J. Immunol.* (1985) 135:2835–2841: Taketani, et al., ibid (1984) 133:816–821; and Vega, et al., *Proc. Natl. Acad. Sci. USA* (1985) 82:7394–7398).

These reports have focused considerable attention on the region between residues 147 and 157, although other regions can also produce functional differences (Ezquerra, et al., *J. Immunol.* (1985) 134:2727–2733). Clusters of variability have been reported at the carboxy-terminal end of the first extracellular domain and at the amino-terminal end of the second extracellular domain (Ways, et al., *J. Biol. Chem.* (1985) 26:11924–11933). Sequences between residues 105–108 of all Class I molecules are related to that of the fibronectin binding tetrapeptide (Auffray and Novotny, *J. Human Immunology* (1986) 15:381–390), which tetrapeptide in either orientation is found to have cell attachment properties (Pierschbacher and Ruoslahti, *Nature* (1984) 309:30–33; Yamada and Kennedy, *J. Cell. Biol.* (1985) 28:99–104). Substitution at position 107 affecting a single monoclonal antibody defined epitope of HLA-A2 has been reported by Salter, et al., *J. Exp. Med.* (1987) 166:283–288.

Copending U.S. patent application Ser. No. 08/222,851 filed Apr. 5, 1994, and PCT Application US95/04349 filed Apr. 5, 1995, each disclose class I MHC peptides which regulate cytotoxic T-cell lymphocyte (CTL) activity. Copending U.S. patent application Ser. No. 07/844,716 filed Mar. 2, 1992, and PCT Application US93/01758 filed Mar. 2, 1993, each disclose lymphocyte activity regulation by HLA peptides. The entire disclosure of each of the above mentioned patent applications is incorporated herein by reference.

DISCLOSURE OF THE INVENTION

Methods and compositions are provided for immunomodulation to inhibit cytotoxic T-lymphocytes ("CTL") from undesirably attacking cells in a host or in vitro. Although the compositions of the invention contain the unnatural"D" forms of amino acids, surprisingly, these compositions exhibit biological activity in modulating the immune system. Inclusion of the unnatural"D" forms is advantageous as it renders the composition less susceptible to degradation in vivo. The compositions include a compound having immunomodulating activity which is a peptide-type compound, or a variant or fragment, including the N-terminal acylated and C-terminal amidated or esterified forms thereof of up to 30 amino acids wherein the peptide-type compound comprises the formula SEQ ID NOS:1 and 2

$$R\ aa^{76\text{-}77}\ L\ aa^{79\text{-}84}$$

or $$aa^{84\text{-}79}\ L\ aa^{77\text{-}76}\ R$$

wherein:

$aa^{76}$ is E or V;

$aa^{77}$ is D, S or N;

$aa^{79}$ is R or G;

$aa^{80}$ is I or N;

$aa^{81}$ is a small or hydrophobic amino acid;

$aa^{82}$ is R or L;

$aa^{83}$ is G or R; and $aa^{84}$ is a small or hydrophobic amino acid;

wherein at least one of the amino acids is the D isomer. The compositions are useful for immunomodulation in vitro and in vivo.

MODES OF CARRYING OUT THE INVENTION

In accordance with the subject invention, CTL immunomodulating compositions are provided which share, at least in part, a sequence present in a Class I HLA-B $\alpha_1$-domain, wherein the sequence is of at least 6 amino acids. The compositions may differ from the naturally occurring HLA-B $\alpha_1$-domain sequences in having substitution of amino acids which do not adversely affect the activity of the peptides, and must include at least one D-isomer.

For the most part, the compounds will be based on a 6 amino acid sequence found at positions 79–84 in the HLA-B sequence and but may include amino acids related to those at HLA-B positions 60 to 84, as well as include tandem repeats and/or irrelevant sequence extensions.

The amino acid sequences indicated above provide for amino acids which are present at the indicated position in one or more naturally occurring HLA-B composition. However, as is well known, conservative amino acid substitutions are permitted while retaining activity.

The compounds of the invention have immunomodulatory activity and have up to 30 amino acids. They are based on the formula SEQ ID NOS:1 and 2

R $aa^{76-77}$ L $aa^{79-84}$ or $aa^{84-79}$ L $aa^{77-76}$ R wherein:

$aa^{76}$, $aa^{77}$, and $aa^{79-84}$ are as defined above; however the invention compounds also include variants and fragments which retain immunomodulatory activity.

In all the compounds of the invention, at least one of the amino acids is the D isomer. Preferably all of the amino acids are in the D form. Surprisingly, these peptide-like compounds retain immunomodulatory activity even though the stereo-chemistry is unfamiliar to the target organism. Some of the compounds are indeed more effective than their corresponding diastereomers or enantiomers.

Some of the compounds may be prepared in substantially pure form. As used herein, the term "substantially pure" means a preparation of the compound which is usually greater than about 70% free of materials with which the peptide may naturally be associated, and preferably greater than about 80% free of these materials; "these materials," however, exclude materials with which the peptide may be mixed in the preparation of pharmaceutical compositions.

By "peptide-type" compound is meant compounds which are derived from amino acid sequences, but wherein optionally one or more of the peptide bonds is replaced by an isostere as further described hereinbelow. Thus "peptide-type" compounds include peptides and compounds wherein an isostere is present.

By "immunomodulating activity" is meant that the compound can be shown to inhibit CTL-mediated lysis in the cytotoxicity assay set forth in Example 1 below and/or inhibits the proliferation of purified T cells in response to anti-CD3 according to the assay described in that example.

The invention compounds also include "variants", i.e., peptide-type compounds which differ from those specifically set forth above by conservative substitutions which do not destroy the immunomodulating activity of the compound.

As to variants, by "conservative substitution" is meant that an amino acid which is of the same general group as that for which substitution is made replaces the referent amino acid. The replacing amino acids may or may not be gene-encoded. They may also include either D or L-isomers where relevant. Thus, conservative substitutions are those within groups defined as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less inclusive of the carboxyl when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at the relevant pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues.

For the naturally occurring protein amino acids, subclassification according to the foregoing scheme is as follows.

Acidic: Aspartic acid and Glutamic acid;

Basic: Arginine, Lysine; Histidine;

Small: Glycine, Serine, Alanine, Threonine; Cysteine

Polar/large: Asparagine, Glutamine;

Hydrophobic: Tyrosine, Valine, Isoleucine, Leucine, Methionine, Phenylalanine, Tryptophan.

The gene-encoded secondary amino acid proline is a special case due to its known effects on the secondary conformation of peptide chains, and is not, therefore, included in a group.

In the present application, either the standard three-letter code or standard one-letter code will be used to denote the gene-encoded amino acids. For the D-isomers, a superscripted dagger (†) to the right of the one-letter code symbol will be employed; thus, D† represents D-aspartic acid, as does D-asp; L† represents D-leucine as does D-leu.

Certain commonly encountered amino acids, which are not encoded by the genetic code, include, for example, beta-alanine (beta-Ala), or other omega-amino acids, such as 3 aminopropionic, 2,3 diaminopropionic (2,3-diaP), 4 aminobutyric and so forth, alpha-aminisobutyric acid (Aib), sarcosine (Sar), ornithine (Orn), citrulline (Cit), t butylalanine (t BuA), t butylglycine (t BuG), N methylisoleucine (N MeIle), phenylglycine (Phg), and cyclohexylalalanine (Cha), norleucine (Nle), 2 naphthylalanine (2 Nal); 1,2,3,4-tetrahydroisoquinoline-3 carboxylic acid (Tic); P 2-thienylalanine (Thi); methionine sulfoxide (MSO); and homoarginine (Har). These also fall conveniently into the above categories.

Based on the above definitions,

Sar, beta-Ala, 2,3-diaP and Aib are small;

t BuA, t BuG, N MeIle, Nle, Mvl, Cha, Phg, Nal, Thi and Tic are hydrophobic;

Orn and Har are basic;

Cit, Acetyl Lys, and MSO are neutral/polar.

Where relevant, the D-isomers of the nongene-encoded amino acids will be denoted by a prefix D- when the nongene-encoded amino acid appears in a sequence generally using the three-letter code; however, a superscripted dagger (†) will be used when the nongene-encoded amino acid appears in a sequence where the gene-encoded amino acids are denoted by a one-letter code.

The various omega-amino acids are classified according to size as small (beta-Ala and 3 aminopropionic) or as large and hydrophobic (all others).

Other amino acid substitutions for those encoded in the gene can also be included in peptide compounds within the scope of the invention and can be classified within this general scheme according to their structure.

In general, the number of substitutions as compared to the basic sequences set forth above to provide variants that come within the scope of the invention will include relatively few substitutions. As previously indicated, even though specific amino acids or a limited number of amino acids have been indicated at each site, individual amino acid substitutions may be made to determine which amino acids are essential. Usually, the number of substitutions will not exceed 20% of the total number of amino acids in the sequence, usually not exceed 15%, more usually not exceed 10%, generally being not more than 3 substitutions, more usually not more than 2 substitutions; and still more usually not more than 1 substitution.

In all cases, the resultant of the substitution or substitutions must retain immunomodulating activity as defined hereinabove.

The amino terminus of the compound may be in the free amino form or may be acylated by a group of the formula RCO-, wherein R represents a hydrocarbyl group of 1–6C. The hydrocarbyl group is saturated or unsaturated and is typically, for example, methyl, ethyl, i-propyl, t-butyl, N-pentyl, cyclohexyl, cyclohexene-2-yl, hexene-3-yl, hexyne-4-yl, and the like.

The C-terminus of the compounds of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

When the compounds of the invention contain basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

In all of the compounds of the invention, one or more peptide linkages (—CO—NH—) may optionally be replaced with another linkage which is an isostere such as -$CH_2NH$-, -$CH_2S$-, —$CH_2CH_2$, —CH═CH— (cis and trans), —$COCH_2$-, —CH(OH)$CH_2$— and —$CH_2SO$—. This replacement can be made by methods known in the art. The following references describe preparation of peptide analogs which include these alternative-inking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, N.Y., p. 267 (1983) (general review); Morley, J. S., *Trends Pharm Sci* (1980) pp. 463–468 (general review); Hudson, D., et al., *Int J Pept Prot Res* (1979) 14:177–185 (—$CH_2NH$—, —$CH_2CH_2$—); Spatola, A. F., et al., *Life Sci* (1986) 38:1243–1249 (-$CH_2$-S); Hann, M. M., *J Chem Soc Perkin Trans I* (1982) 307–314 (—CH—CH—, cis and trans); Almquist, R. G., et al., *J Med Chem* (1980) 23:1392–1398 (—$COCH_2$—); Jennings-White, C., et al., *Tetrahedron Lett* (1982) 23:2533 (—$COCH_2$—); Szelke, M., et al., European Application EP 45665 (1982) CA:97:39405 (1982) (—CH(OH)$CH_2$—); Holladay, M. W., et al., *Tetrahedron Lett* (1983) 24:4401–4404 (—C(OH)$CH_2$—); and Hruby, V. J., *Life Sci* (1982) 31:189–199 (—$CH_2$-S—).

Preferred as the basis for α and/or β in the above formula are peptides from HLA-B0701 (B7) or B2702, where one or more amino acids may be substituted while retaining CTL modulating activity. The portions of B0701 (B7) and B2702 at positions 75–84 differ at sites 77, 80, 81, 82 and 83, having identity at sites 75, 76, 78, 79, and 84. It is found that the amino acid at sites 77, 81 and 84 may be substituted without loss of immunomodulating activity. Thus, a consensus sequence is $REX^1LRX^2X^3X^4X^5X^6$ (SEQ ID NO:3), where $X^1$ may be any amino acid, polar or non-polar, preferably polar, either charged or uncharged; $X^2$ is preferably an amino acid of at least five carbon atoms, which may be polar or non-polar, particularly asparagine and isoleucine; $X^3$ may be non-polar aliphatic of from two to six carbon atoms (i.e., hydrophobic or small), more particularly three to five carbon atoms, especially isoleucine; $X^4$ may be any amino acid, particularly aliphatic, either charged or uncharged, preferably at least about five carbon atoms, such as arginine and leucine; $X^5$ may be any amino acid, preferably aliphatic, charged or uncharged, polar or non-polar, particularly glycine and arginine, more particularly one of $X^4$ and $X^5$ is arginine. $X^6$ is any amino acid, preferably hydrophobic or small. Preferably, $X^{1-6}$ will be S, N, L, R, G, Y or N, I, A, L, R, Y or D, I, L, L, R, Y, respectively, where one of the amino acids in one group may be substituted at the same site for the amino acid in the other group.

The sequences may be extended at either or both the N- or C-terminus by additional amino acids in the HLA sequence or by other amino acids, which do not interfere with the activity of the defined peptides.

The compounds of the invention will have at least 6 amino acids, more usually at least 8 amino acids, generally at least 10 amino acids, preferably at least about 12 amino acids or more, generally being not more than 30 amino acids, more usually not more than about 25 amino acids. Fragments included within the invention contain at least the portion $aa^{79-84}$ or $aa^{84-79}$.

Preferred compounds include (SEQ ID NOS:4 through 11)

R†IALY
R†I†A†L†S†
RILL†RY
R†I†L†L†R†Y†
SLAI†R
Y†L†A†I†R†
SRLL†IR
Y†R†L†L†I†R† and the extended, N-terminal acylated and C-terminal amidated or esterified forms thereof The subject compounds may be modified in a wide variety of ways. The peptides may be joined by covalent bonds at any convenient site along the peptide to a variety of other compounds for different purposes. Thus, the peptides may be joined to immunogens for administration to a host for immunization for production of antibodies, or may be joined to a noN-adjacent MHC sequence of the particular MHC antigen by means of synthesis, expression of a synthetic gene, or the like; joined to a lipid or polyalkyleneoxy group; joined to a sugar; or joined to a nucleic acid. Of particular interest is joining the subject peptides to another peptide by synthesis or expression of a synthetic gene where the other peptide provides for extended stability of the subject peptides when administered to a host. Various peptides may be used, such as the immunoglobulin constant region, e.g., IgG Fc. Alternatively, the subject peptides may be joined to a toxin, such as diphtheria toxin, ricin, abrin, and the like, particularly where the binding chain has been removed or inactivated, so as to prevent noN-specific binding of the binding chain to cells.

The sequences may be modified in a variety of ways depending upon their ultimate purpose. Different N- or C-terminal groups may be introduced which allow for linking of the peptide to solid substrates or other molecules. In a synthetic procedure, any molecule may be introduced at the N- or C-terminus which would allow for subsequent reaction, depending upon the purpose for which the peptide is prepared.

For diagnostic purposes, a wide variety of labels may be linked to the terminus, which may provide, directly or indirectly, a detectable signal. For example, fluorescers may be introduced at the terminus or other molecules which provide a linkage to labels such as fluorescers, enzymes, particles, or the like. For example, linkage may be introduced at the terminus, e.g., biotin, which will bind to an avidin conjugate with enzymes or fluorescers. Alternatively, various reactive sites may be introduced at the terminus for linking to particles, solid substrates, macromolecules, or the like. For example, an internal amino moiety of a growing chain bound to a solid substrate with the intermediate side groups protected, may be conjugated with methyldithiobenzoic acid (MDTB). The free mercaptan group may then be used for conjugating with activated olefins. Thus, proteins, such as serum albumin, keyhole limpet hemocyanin, bovine β-globulin, or the like, may be conjugated to the peptide to provide for an immunogen to produce antibodies to the peptide for use in immunoassays, for affinity chromatography, or the like. Alternatively, the peptide can be bonded to another polypeptide by preparing a DNA sequence which has the peptide at the N-terminus, C-terminus or internal to the protein, so as to provide a fused protein which includes the binding peptide of interest. In this manner, fused proteins may be produced which have enzymatic activity, which enzymatic activity may be modulated by macromolecules, e.g., antibodies, binding to the peptide of interest. Thus, the peptides of the subject invention may be modified in a wide variety of ways for a variety of end purposes while still retaining biological activity. (By "biological activity" is intended the ability to bind with specific affinity ($>10^6$ $M^{-1}$) to an antibody to the same epitope of the native protein.)

The subject peptides may also be used in combination with antigenic peptides or proteins of interest to activate CTL's. Thus, the subject peptides may be bound to a protein, either directly or indirectly, so as to be able to present two epitopes to the CTL to which the CTL may bind and be activated. Of particular interest, is where the subject peptides may be bound to a liposome or a bilayer lipid membrane in conjunction with a peptide or protein providing the other determinant site.

Various techniques are available for joining a peptide or protein to a lipid, particularly a phospholipid to provide for the presence of the peptide or protein on the liposome surface. Phosphatidyl choline, phosphatidyl ethanolamine, or other lipid may be used with a bifunctional linking agent, such as MBSE, glutaraldehyde, methyldithiobenzoic acid, or the like. The formation of liposomes with conjugated proteins finds ample support in the literature, see, for example, U.S. Pat. NOS. 3,887,698; 4,261,975 and 4,193,983. The modified peptide or protein is combined with the lipids in an aqueous medium and sonicated to provide the desired liposomes. The liposomes may then be harvested and used in the ways indicated.

Formulation and Use in Transplantation and Autoimmune Suppression

The immunomodulating activity of the compounds of the invention makes them useful in preventing rejection of transplants and in the treatment of autoimmune diseases. While for the most part allogeneic implants will be involved, there is substantial interest in using xenogeneic sources of organs, such as pig, primate other than human, e.g., baboon, etc. Organs of interest include heart, lung, kidney, vascular vessels, eye, gut, bone marrow, liver, etc.

For transplantation, the organ may be initially bathed in one or more compounds according to the subject invention, which may be used individually or in combination with other drugs. Generally, the concentration for the subject compound will depend upon its particular activity, generally being in the range of about 0.1 µg/ml to 1 mg/ml. The subject compositions, regardless of the treatment of the transplant, may be administered to the recipient host directly. Particular peptides act on CTLs having a broad range of Class I MHC antigens. These compounds find particular application in protecting against transplantation rejection by providing for a regimen, where the peptides are administered at various times and in various periods, depending upon whether a bolus, slow release, a depot, continuous infusion or other form of dosage is employed; the manner of administration, whether oral, parenteral, inhalation, or the like; the particular times chosen for the administration; the degree of difference between the transplantation antigens of the donor and recipient; and the like.

The administration of the peptide may be prior to, at and subsequent to the day of transplantation, or combination thereof It is found that various regimens may be employed effectively, so that no particular regimen can be specifically defined. If the peptide is administered prior to the transplantation, administration should begin at least three days prior to the transplantation, preferably at least about five days, and more preferably at least about 7–20 days prior to the transplantation, while if the peptide is administered beginning at or after the transplantation, preferably administration is initiated within one day of the transplantation, preferably on the day of the transplantation, and may be administered during the grafting process. Usually there will be multiple administrations, usually not more than about 10, more usually not more than about 6, generally at least about 2, frequently ranging from about 2 to 6 administrations, where the administrations may be daily, alternating days, usually at not more than about 3 days, preferably not more than 2 day, intervals.

While multiple daily dosages may be given, it is found that a single dose per day will suffice. Therefore, overall the regimen will involve administrations during the period 20 days prior to the grafting operation and up to about 10 days subsequent to the grafting operation. There will usually be an initial dose beginning in the period −20 to +1 days, where (−) intends prior to the day of operation and (+) intends subsequent to the day of operation, with 0 being the day of operation. Preferably, the initial dose will be not earlier than 7 days prior to the operation, where the administration is primarily prior to the operation and not more than 1 day after the operation, where the initial dose is after the operation. If desired, administration may be continued during the life of the implant.

As part of the regimen, an immunosuppressant drug can also be administered, generally at or subsequent to the transplant, either by itself, or in conjunction with the peptide, particularly where the peptide is administered after the transplantation. A subtherapeutic dose of the immunosuppressant compound is employed, where the immunosuppressant may be a single agent or a combination of agents, where the combination is below a subtherapeutic dosage. By subtherapeutic dosage is intended that in the absence of the peptide, the graft would be rejected in a majority of patients within 100 days, usually within 30 days, and more usually within 20 days. Various immunosuppressants are known, such as cyclosporin A, FK506, antibodies for plasma membrane proteins associated with graft rejection, such as antibodies to CD4, CD8, CD2, LFA-1, ICAM-1, CD28, and the like.

The subtherapeutic dose will be not less than about 5% of the therapeutic dosage, usually not less than about 10%, more usually not less than about 25%, and usually not greater than about 75%, more usually not greater than about 60%. Where combinations are used, the subtherapeutic dosage is primarily directed to the drug(s) which have significant side effects, although there is a substantial interest in minimizing the effect on the immune system. In referring to a subtherapeutic dosage, is intended a bolus amount, since a direct comparison is difficult, where the subject regimen is terminated within a short period of the transplantation. The subject regimen may be daily or less than daily, and other regimens may involve repetitive daily administrations. Suffice it to say, that the subject regimen may be terminated within about 20 days, usually within about 10 days of the transplantation, as contrasted with other immunosuppressant regimens, which are for the life of the patient.

Generally, the amount of peptide administered will be in from about 0.1–50, more usually from about 1–25 mg/kg of host. This amount will be used for a peptide compound where the half life of the peptide compound is fewer than six hours, more particularly fewer than four hours and greater than about one minute. Dosages in the lower portion of the range and even lower dosages may be employed, where the peptide has an enhanced half-life or is provided as a depot, such as a slow release composition comprising particles, introduced in a matrix which maintains the peptide over an extended period of time, e.g., a collagen matrix, use of a pump which continuously infuses the peptide over an extended period of time at a substantially continuous rate, or the like.

Depending upon the time at which the peptide is administered prior to the transplantation, the immunosuppressant regimen may vary. For example, where the peptide is given at −7 and −1 day, a single subtherapeutic dosage of cyclosporin A may have insignificant protective capability, while administering cyclosporin A daily, 0–4 days, can be protective. A regimen of administration of peptide on days −14, −12, −10 and −7 followed by cyclosporin A on days 0–4 after transplantation can also have substantial protective effect. Alternatively, by using a combined dosage of the peptide and a subtherapeutic dosage of cyclosporin A, on days 0–4 after transplantation, retention of the grafts can be greatly enhanced.

The subject compositions can be prepared as formulations for direct administration, where the compositions may be in a physiologically acceptable medium. Where other drugs are present, specialized formulations may be employed to ensure the stable dispersion of the other drug. Media which may be employed include water, saline, phosphate buffered saline, ethanol, vegetable oil, etc. Where cyclosporin is involved, the formulation may also include Cremaphor®. Other conventional media may also find use. In addition, other components may also be included, such as stabilizers, antibiotics, detergents, dispersants, emulsifying agents, liposomes, etc.

In general, similar formulations can be used and optimized for use in protocols for treatment of autoimmune diseases. Such treatments can be routinely designed and optimized based on standard medical practice and based initially, at least, on animal models. There are animal models for a number of autoimmune diseases, for example, NOD mice are widely used as murine models for the investigation of autoimmune diabetes, as they spontaneously develop diabetes by about eight weeks of age. Various peptides derived from B2702.75–84 are currently being tested in protocols involving three ip injections per week starting at three weeks of age. The results of these models will be helpful in the design of appropriate therapeutic protocols for diabetes. Similar models are useful in the development of protocols for other autoimmune diseases, such as rheumatoid arthritis and lupus erythematosis.

Synthesis

The subject compositions can be produced in a variety of ways. Since the peptide-type compounds of the invention contain at least one D-amino acid, standard peptide synthesis methods, either solid phase or solution phase, are preferred. Automated synthesizers may be used, e.g., Beckman, Applied Biosystems Inc., etc. Portions of the compounds which contain only the gene-encoded amino acids and contain only peptide linkages can be prepared using standard recombinant techniques, and these portions ligated to D-amino acids or other non-gene enclosed amino acids. In such methods, expression systems are constructed using conventional methods wherein a nucleotide sequence encoding the desired peptide is operably linked to control sequences capable of effecting its expression in suitable host cells. A wide variety of host cells can be used, including prokaryotes, yeast, mammalian cells, avian cells, insect cells and plant cells. The choice of appropriate control sequences will, of course, be governed by the choice of recombinant host. In order to produce the peptide, the recombinant cells modified to contain a DNA molecule which comprises the desired expression system are cultured under conditions wherein the desired peptide is produced and the peptide is recovered from the culture. Standard purification processes can be used for recovering the peptide or cell supernatants or lysates may be used in crude form for subsequent ligation in some circumstances. In one embodiment, the expression system can be designed to include multiple copies of the nucleotide sequence encoding the desired portion of the compound in tandem separated by an amino acid, such as methionine, which will allow for cleavage at the Met residue, whereby the subject portions may be isolated. Amino acid sequences that are substrates for proteolytic enzymes may also be used to separate the portions in the encoded tandem protein.

Antibodies

Antibodies that are "specifically immunoreactive" or "immuneospecific" for with the peptide-type compounds of the invention may also be prepared. By "specifically immunoreactive" is meant antibodies which react with the compounds of the invention, but fail to react with the native peptides represented by the sequences in the HLA alleles upon which the D-isomer containing compounds are based. For preparation of these antibodies, standard immunization techniques may be employed whereby a suitable animal is administered the compound to which an antibody is desired, and administration is continued under appropriate protocols until suitable titers of the desired antibodies are found in the serum or plasma. It may be necessary to associate the immunogen with an appropriate carrier in order to provide sufficient titers, as is understood in the art. For some purposes, the antisera may be used directly; for other uses, it may be desirable to purify the immunoglobulin fraction or to prepare monoclonal forms of these antibodies with the appropriate specificities. For the preparation of monoclonal antibodies, appropriate antibody-producing cells such as splenocytes or peripheral blood lymphocytes are harvested and immortalized, typically by polyethylene glycol fusion with tumor cells, and the resulting immortalized cells are cultured individually and screened for the production of the desired antibodies. The antibodies prepared as described above can be used intact, or fragments thereof may be used which retain their immunospecificity. Typical such fragments are $F_{ab}$, $F_{ab'}$, or $F_{(ab')2}$ fragments.

In addition, the antibodies may be prepared using standard recombinant techniques by recovering the relevant genes from the immortalized cells. Under these circumstances, the genes may also be manipulated to provide the above-mentioned fragments, or to provide the antibodies in polyvalent form by coupling a heavy chain/light chain combination immunospecific for one of the peptides of the invention with a similar combination immunospecific for another entity. Alternatively, the antibodies may be prepared in single-chain forms such as $F_v$ forms. Various additional modifications, such as humanization of murine-derived antibodies may also be made.

Antibodies with immunospecificity for the peptide-type compounds of the invention are useful in purifying these peptides, as diagnostic tools in quantitating the peptides of the invention, and in diagnostic assays tracing the activity of the peptide-type compounds of the invention in vivo.

The following examples are offered by way of illustration and not by way of limitation.

EXAMPLE 1

Assay for Immunomodulating Activity

The compounds of the invention can be assessed for their ability to modulate the immune system by convenient in vitro assays. The following example illustrates these assays and provides results for compounds of the invention and for control peptides. In this example, the various peptides were tested for their ability to inhibit lysis by established CTL, for the ability inhibit proliferation of purified T cells in response to anti-CD3, and for their ability affect intracellular calcium levels. The following paragraphs describe p reparation of the various materials used in the assay and certain features of the assays as conducted.

Matrials and Methods

Cells and Cell Culture

PBL were isolated from normal donors by centrifugation over Ficoll-Hypaque. In some cases, T cells were purified from this preparation using the method of Secrist et al. [*J Exp. Med.* (1993) 178:2123]. Briefly, cells isolated over Ficoll-Hypaque were incubated for 1 hour in Petri dishes. Nonadherent cells were passed over a nylon wool column and the resulting population was >90% CD3+ by FACS analysis. CD8+ CTL lines specific for HLA-A2, B7, B27, B48, or Cw4 were generated and maintained in long-term culture as previously described [Buxton et al., *J Exp. Med.* (1992) 175:809; Wesley et al., *Hum. Immunol.* (1993) 36:149]. Jurkat E6-1 and the T cell receptor negative Jurkat, JRT3-T3.5, were obtained from the American Type Culture Collection (ATCC; Rockville, Md.). Other cell lines used included the EBV transformed B cell lines JY, MS, CIR, and 721.221; K562 and HEL, erythroleukemia cell lines; the T cell tumors Peer, Hut-78 and HSB; the Burkitt's lymphoma cell lines Daudi and SUP B17 [Wright et al., *J Exp. Med.* (1989) 169:1557], and the NK-like cell line YT2C2. All transformed cells were grown in culture medium [RPMI-1640 supplemented with 10% fetal bovine serum (Hyclone, Inc., Logan, Utah) 2 mM L-glutamine, 100 U/ml penicillin, and 100 µg/ml streptomycin].

Cytotoxicity Assay

CTL assays were performed as described using $^{51}$Cr-labeled EBV transformed B cells expressing the appropriate HLA allele as targets [Krensky et al., *J. Immunol.* (1982) 129:2001].

Proliferation Assay $10^5$ cells were added to microtiter wells that had been coated with anti-CD3 (Sigma, St. Louis, Mo.) at 5 µg/ml. Plates were incubated at 370 in 5% $CO_2$. After 48 hours, 1 µCi[$^3$H]-thymidine was added to each well. Plates were harvested on a PHD Cell Harvester 24 hours later and [$^3$H]-thymidine incorporation determined by scintillation counting.

Peptides

Peptides were synthesized with an Applied Biosystems Miligen/Biosearch 9050 automated peptide synthesizer using Fmoc chemistry in the Protein and Nucleic Acid Facility at Stanford Medical Center. Peptides were purified by HPLC and the homogenicity of each was confirmed by analytical reverse-phase HPLC. Amino acid content was confirmed by amino acid analysis. Peptides were dissolved at 40 mg/mil in DMSO and then further diluted into culture medium for assay.

RESULTS

The following peptides were prepared for testing:

TABLE 1

Amino acid sequences of synthetic peptides. (SEQ. ID. NOS: 12 and 28)

| PEPTIDE | 75 | 76 | 77 | 78 | 79 | 80 | 81 | 82 | 83 | 84 |
|---|---|---|---|---|---|---|---|---|---|---|
| B2702.75-84 | R | E | N | L | R | I | A | L | R | Y |
| B2705.75-84 | — | — | D | — | — | T | L | — | — | — |
| B7.75-84 | — | — | S | — | — | N | L | R | G | — |

TABLE 1-continued

Amino acid sequences of synthetic peptides. (SEQ. ID. NOS: 12 and 28)

| PEPTIDE | 75 | 76 | 77 | 78 | 79 | 80 | 81 | 82 | 83 | 84 |
|---|---|---|---|---|---|---|---|---|---|---|
| B2702.75-84D[77] | — | — | D | — | — | — | — | — | — | — |
| B2702.75-84T[80] | — | — | — | — | — | T | — | — | — | — |
| B2702.75-84L[81] | — | — | — | — | — | — | L | — | — | — |
| B2702.84-75/75-84 | Y R | L A | I R | L N | E R | R E | N L | R I | A L | R Y |
| B7.84-75/75-84 | — G | R L | N — | — S | — — | — — | S — | — N | L R | G — |
| B2702.84-75T/75-84 | — — | — — | T — | — — | — — | — — | — — | — — | — — | — — |
| B2702.84-75/75-84T | — — | — — | — — | — — | — — | — — | — — | T — | — — | — — |
| B2702.84-75T/75-84T | — — | — — | T — | — — | — — | — — | — — | T — | — — | — — |
| B2702.84-75/84-75 | — — | — — | — — | — — | — — | Y R | L A | I R | L N | E R |
| B2702.60-84 | W D | R E | T Q | I C | K A | K A | Q T | D — | — — | — — |
| B2702.70-84 | — — | — — | — — | — — | K A | Q T | D — | — — | — — | — — |
| B7.75-84 | — — | — — | — S | — — | N L | R G | — — | — — | — — | — — |
| B7.84-75/75-84 | — G | R L | N — | — S | — — | — — | S — | — N | L R | G — |
| B2702.84-79/79-84 | Y R | L A | I R | — — | — — | — — | — — | — — | — — | — — |

Dashes indicate identity with the residue found in the B2702.75-84 or B2702.84-75/74-84 sequences.

Inhibition of Lysis by Established CTL as a Function of Amino Acid Sequence

A. Focused Substitutions

It has previously been shown that HLA-B2702.60–84 inhibits lysis by established CTL (Clayberger et al. *Transplant Proc* (1993) 25:477, whereas HLA-B2705.60–84 does not.

In the present protocol, a CD8+ CTL line specific for HLA-A2 was tested in the presence of various peptides for lysis of $^{51}$Cr-labeled JY targets. Peptides were added to a final concentration of 100 $\mu$g/ml at the initiation of the 4 h assay. Each determination was the mean of triplicate wells. Similar results as those described below were obtained using CTL specific for HLA-B27 or -B48.

HLA-B2702.75–84 inhibited lysis by established CTL in this assay. However, B2702.60–84 was approximately 5 fold more potent than B2702.75–84, based on the concentration required to achieve 50% inhibition of cytotoxicity. Peptides were therefore prepared to evaluate the effect of peptide length. The 15-mer, HLA-B2702.70–84 was comparably effective in inhibiting cytolysis to B2072.75–84. However, an inverted repeat dimer, B2702.84–75/75–84 (YRLAIRLNERRENLRIALRY) (SEQ ID NO:12) was as potent as B2702.60–84 in terms of concentration required to achieve 50% inhibition of cytolysis (approximately 3 $\mu$M) and was superior to this peptide in that it completely inhibited cytolysis. B2702.75–84/75–84 showed similar activity.

The effect of replacing individual amino acids in the immunomodulating peptides was then tested. The peptide 02.75–84L$^{81}$, wherein leucine replaces alanine at position 81, inhibited lysis comparably to 02.75–84. However, 02.75–84D$^{77}$ wherein aspartic replaces asparagine at position 77, and 02.75–84T$^{80}$, wherein threonine replaces isoleucine at position 80 did not inhibit lysis. It appears that the Ile residue at position 80 of B2702 is critical in that its replacement with threonine results in complete loss of inhibition activity; the effect of replacing asparagine at position 77 appeared less dramatic.

With respect to the dimers of the invention, substitution of either of the Ile$^{80}$ residues in the inverted repeat with threonine completely abrogated inhibition. Synthetic peptides corresponding to B7.75–84 or B7.84–75/75–84 did not inhibit CTL-mediated lysis at any concentration tested.

B. Serine Scan

In addition, the dimers B2702.84–75/75–84 and B2702.84–79/79–84 were "scanned" by substituting serine for the native residue on both sides of the dimer in each position in turn. When tested in this assay for inhibition of lysis by established CTL, only those dimers wherein serine was substituted for the isoleucine at position 80 and/or the leucine at position 78 and/or 82 no longer had activity. Substitution of serine at other locations in the molecule was without significant effect. The technique of systematically replacing corresponding amino acids in the dimer with serine residues then testing for activity is referred to as a "serine scan."

C. Substitution with D-amino Acids

In these determinations, inhibition of cytolysis as described above employed the CTL cell line AJY, a long term CD8+ CTL line specific for HLA-A2 and the target cell was the B-lymphoblastoid cell line JY (HLA-A2, B7). The cytotoxicity assay was performed as described by Clayberger et al., *J Exp. Med.* (1984) 162:1709–1714; and Reiss et al., *Proc Natl Acad Sci USA* (1980) 77:5432–5436. The peptides were preincubated for 30 min with 1–3x10$^3$ CTLs before addition of 10$^3$ $^{51}$Cr-labeled B-lymphoblastoid target cells. The results are reported for varying concentrations of the peptide with varying ratios of the two cell lines.

TABLE 2

| | % Specific Lysis Peptide conc $\mu$g/ml | | | | | |
|---|---|---|---|---|---|---|
| | 200 | | 100 | | 25 | |
| Cell ratio | 10:1 | 1:1 | 10:1 | 1:1 | 10:1 | 1:1 |
| DMSO | 80.1 | 31.2 | 79.9 | 27.9 | 77.5 | 34.2 |
| 2702.60-84 (L-isomer) | 26.8 | 11.5 | 35.7 | 15.7 | 38.0 | 24.9 |
| 2702.75-84 (L-isomer) | 33.1 | 16.4 | 43.7 | 18.6 | 60.9 | 23.9 |
| 2702.75-84 (D-isomer) | 16.0 | 11.6 | 17.1 | 1.3 | 39.2 | 12.2 |
| 2705.60-84 (L-isomer) | 67.4 | 29.8 | 59.9 | 29.4 | 73.7 | 27.8 |

Thus, the peptide representing B2702.75–84 wherein all of the residues were replaced by the D-isomer appeared even more active than B2702.60–84 in the native L-amino acid form.

D. Free Peptide Required

Effectiveness in inhibition appeared dependent on providing the peptide as such, rather than as a cellular-bound HLA molecule. Previous work from our group had demonstrated that HLA molecules expressing the Bw4a motif could be recognized by Bw4 specific CTL [Clayberger et al., *J. Immunol.* (1990) 144:4172]. Therefore, two different types of experiments were used to determine whether cell surface HLA molecules expressing the Bw4a determinant could inhibit lysis by CTL specific for HLA-A2. First, transfectants expressing HLA-B2702 were used as cold target inhibitors of HLA-A2 specific CTL. Alternatively, transfectants expressing both HLA-A2 and HLA-B58, an allele that is Bw4a+, were used as targets for HLA-A2 specific CTL. No inhibition of HLA-A2 specific lysis was observed in either case, indicating that the Bw4a sequence is inhibitory only in soluble form.

Inhibition of T cell Proliferation

A. Focused Substitutions

Peptides were evaluated for effects on the proliferation of purified T cells stimulated by immobilized anti-CD3 antibody. B2702.84–75/75–84 inhibits this proliferation as measured by decreased incorporation of $^3$H-thymidine, but B2702.75–84 and B7.75–84 do not. When the inverted repeat B2702.84–75/75–84 is substituted in either or both of the Ile$^{80}$ residues with Thr, proliferation was not inhibited. Similar results were obtained with the 2702.84–79/79–84.

B. Serine Scan

A serine scan of these dimers (B2702.84–75/75–84 and B2072.84–79/79–84) according to the technique described in Example 1 showed that activity in the foregoing proliferation assay was significantly diminished or abolished only when both Ile residues at position 80 and/or both Leu residues at positions 78 and/or 82 were replaced.

C. Substitution with D-amino Acids

To measure the effect of D-substitution on proliferation, PBL from normal donors were cultured at 5×10$^5$ cells/round bottom microtiter well in RPMI-1640 supplemented with 10% fetal bovine serum and L-glutamine. Cultures were supplemented with Conagglutinin A. Cells were incubated at 37° C. for three days at which point $^3$H-thymidine (1μCi/well) was added. After 24 hours, wells were harvested and $^3$H-thymidine incorporation determined by scintillation counter. The following table indicates the results:

TABLE 3

|  | 200 | | 50 | |
| --- | --- | --- | --- | --- |
| Peptide conc μg/ml | 3 | 1 | 3 | 1 |
| Con A conc mg/ml | | CPM ± SD | | |
| DMSO | 45,165 ± 2885 | 17,884 ± 1658 | 46,534 ± 2246 | 16410 ± 1314 |
| B2702.75-84 (L-isomer) | 20,905 ± 2047 | 2,322 ± 147 | 32,618 ± 1582 | 5,806 ± 721 |
| B2702.75-84 (D-isomer) | 29,114 ± 7738 | 6,823 ± 1363 | 40,371 ± 3067 | 12,710 ± 1910 |
| B2702.60-84 (L-isomer) | 43,487 ± 2269 | 12,217 ± 879 | 45,292 ± 1947 | 13,886 ± 2659 |

The results in Table 3 are only approximate since the purity of the various peptides had not been established.

D. Mechanism Studies

Addition of recombinant IL-2 to T cells stimulated by anti-CD3 antibody in the presence of these peptides does not reverse inhibition, indicating that the mechanism underlying unresponsiveness was not "classical" T cell anergy as originally defined by Jenkins and Schwartz [Schwartz et al., Cold Spring Harb. *Symp. Quant. Biol.* (1989) 2:605; Jenkins et al., *Adv. Exp. Med Biol.* (1991) 292:167].

The lack of CTL lysis and T cell proliferation observed in the presence of the B2702.84–75/75–84 peptide was not due to T cell death or apoptosis. T cell lines and freshly isolated peripheral blood lymphocytes were cultured with 1–50 μM peptide. Aliquots of these cultures were stained with propidium iodide and evaluated by FACS for fluorescence. No decrease in the total number or percent viable cells in culture was detected over a one week period.

EXAMPLE 2

Prevention of Allograft Protection in a Rat Model

Materials and Methods

Animals

Adult male, specific pathogen free ACI (RT1$^a$), PVG (RT1$^c$), Brown Norway (BN) (RT1$^n$), and Lewis (Lew) (RT1$^1$) rats, weighing 200–250 grams, were used in these studies. The rats were purchased from Bantin and Kingman, Fremont, CA (PVG) or Charles River, Boston, Mass. (ACI, BN and Lew). ACI rats served as recipients of heart or skin allografts from BN or Lew donors. Animals were maintained in the Falk Cardiovascular Research Building under standard conditions according to institutional guidelines.

Peptides

Peptides were synthesized at the Protein and Nucleic Acid Facility, Beckman Center, Stanford University School of Medicine, or by Multiple Peptide Systems (San Diego, Calif.) by an automated peptide synthesizer using Fmoc chemistry. Peptides were purified by preparative reverse phase HPLC and shown to be >98% homogeneous by analytical reverse phase HPLC. Amino acid content was confirmed by amino acid analysis.

Limiting Dilution Assay for CTL Precursors

The effect of peptides on CTL precursor frequencies in splenocytes was tested as follows. Limiting dilution analysis was carried out essentially as described (Moeller et al. 1993, supra; Skinner and Marbrook. *J. Exp. Med.* (1976) 143:1562). Briefly, spleens were removed from naive animals or from animals that had received an allograft a minimum of 60 days earlier and then teased into a single cell suspension. Responder cells were plated from 1000 to 40,000 cells per well (24 replicates per concentration) into round bottom microliter wells in RPMI 1640 supplemented with 10% fetal bovine serum (Hyclone, Logan, Utah), 2 mM L-glutamine, 5×10$^5$M μ-mercaptoethanol, 100 U/ml penicillin, 100 μg/ml streptomycin, 20% supernatant from Concanavalin A activated rat spleen cells, and 50 μM α-methyl mannoside. Then, 5×10$^5$ irradiated (2000 rads) stimulator cells were added to each well and plates were incubated in a humidified CO$_2$ incubator. After 5 days, aliquots were removed and tested for lysis of $^{51}$Cr-labeled Concanavalin A activated blasts. Aliquots of supernatant were counted in a gamma counter and CTL precursor frequency determined by linear regression (Skinner and Marbrook. 1976, supra). Wells were considered positive if specific release was >10%.

Lymph Node Proliferation Assay

ACI or PVG rats (200 g) were injected intravenously with peptides dissolved in saline on day 0. On the indicated days thereafter, the left rear footpads of the rats were injected with 5×10$^6$ splenocytes from a syngeneic donor and the right rear footpads with 5×10$^6$ splenocytes from an allogeneic Lew donor (Moeller etal. *Transplantation* (1993)55:650). See also Twist and Barnes *Transplantation* (1973) 15:182;

Fanslow et al. Science (1990) 248:739). Seven days after the footpad injection, the animals were sacrificed and the popliteal lymph nodes removed. A single cell suspension was prepared, and the cell number determined using a hemocytometer.

Organ Transplantation

Vascularized cardiac allografts were heterotypically transplanted into the abdomen of recipient rats using a modification of the technique of Ono and Lindsay (Ono and Lindsey *J. Thorac. Cardiovasc. Surg.* (1969) 57:225). Abdominal allografts were palpated on a daily basis to assess graft function, and rejection was deemed complete when palpable ventricular contractions ceased.

Full thickness skin grafts were performed using a modification of the technique described by Billingham and Medawar (*J. Exp. Biol.* (1951) 28:385). Both donor and recipient were shaved and the donor skin was cut in standard 2×2 cm pieces and subdermal fat was surgically removed. Multiple grafts were obtained from a single donor, preserved in cold saline and transplanted on the same day. A piece of skin the same size as the donor graft was removed from the flank of the recipient and any loose connective tissue was surgically removed from the fascia. The allograft was then fashioned to the recipient fascia with a 4-0 vicryl suture. One layer of rough gauze and eight layers of fine gauze sponge were sewn to the recipient skin and fascia around the graft using a 2-0 vicryl suture, securely immobilizing the donor skin to the recipient fascia and allowing the graft to be revascularized. On post-operative day 6 the dressing was removed and the allograft was then inspected for evidence of rejection on a daily basis. Rejection was manifested by erythema, continuous serous exudation, ulceration or allograft necrosis.

Immunosuppression

Cyclosporin A (CsA, Sandoz Pharmaceuticals Corporation, Base, Switzerland) dissolved in olive oil was given orally through a gavage tube at the indicated dose. Peptides were dissolved in water or saline and given intravenously or by gavage as indicated.

Statistical Analyses

Student t-tests were calculated using the Graphpad InStat statistics program to compare allograft survival in different groups. Differences were considered significant if the p value was <0.05.

RESULTS

A. Effect of In Vivo Administration on CTL Differentiation In Vitro-Limiting Dilution Assay for CTL Precursors Initial studies showed that both the B7.75–84 and B2702.75–84 peptides, but neither the A2.75–84 peptide nor a peptide corresponding to the same residues from a rat MHC class I molecule, RT1$^a$, blocked the differentiation of rat splenocytes into allospecific CTL in vitro. Therefore, we tested whether splenocytes obtained from rats treated with the peptides in vivo could differentiate into CTL ex vivo. In preliminary studies, the half-life of the B7.75–84 peptide was determined to be 2–3 hours in rats. Thus, we elected to administer 2–20 mg peptide (6–60 mg/kg) per dose, an amount that is comparable to the dose of the undecapeptide CsA, (10–20 mg/kg).

PVG (RT1$^c$) or ACI (RT1$^a$) rats were treated with a single intravenous injection of saline or 2 mg of A2.75–84, B7.75–84, B2702.75–84, or RT1$^a$.75–84 peptide. Their spleens were removed on different days after peptide treatment, cultured under limiting dilution conditions for 5 days with irradiated (2000R) splenocytes from Lewis rats; i.e., Lew (RT1$^l$) stimulator cells, and assayed for lysis of $^{51}$Cr-labeled Lew blasts. CTL precursor frequency was determined by linear regression analysis. As shown in Table 4, the precursor frequency of Lew specific cells in splenocytes isolated from PVG rats (2/group) treated with either saline, the A2.75–84 peptide, or the RT1$^a$.75–84 peptide was approximately 1 in 55,000, independent of the day on which the spleen was removed. The same frequency was found in splenocytes from animals that had been treated with either the B7.75–84 or B2702.75–84 peptide on the day of splenectomy or 24 hours earlier. However, splenocytes obtained from rats treated with the B7.75–84 or B2702.75–84 peptide 7 or 10 days prior to splenectomy showed an 8–10 fold decrease in the precursor frequency of Lew specific CTL.

TABLE 4

CTL Precursor Frequencies in Splenocytes Isolated from Rats Following Injection of Saline or Various Peptides

| Time after Peptide Injection (days) | Saline | A2.75-84 | RT1A.75-84 | B7.75-84 | B2702.75-84 |
|---|---|---|---|---|---|
| | | [CTL precursor frequency]$^{-1}$ | | | |
| 0 | 54,631 | 55,467 | 56,583 | 55,467 | 54,631 |
| 1 | 55,467 | 55,467 | 54,631 | 55,467 | 54,631 |
| 7 | 56,583 | 54,631 | 55,647 | 567,004 | 465,572 |
| 10 | 54,631 | 55,467 | 56,583 | 634,983 | 468,071 |

Thus, in conclusion, both B7.75–84 and B2702.75–84, when injected into rats, resulted in splenocytes which were not responsive to allogenic challenge in vitro. Neither A2.75–84 nor a control peptide had this effect.

B. Effect on Alloreactivity In Vivo-Lymph Node Proliferation Assay

To assess whether the peptides could affect alloreactivity in vivo, we tested their effects on the accumulation of cells in the draining lymph nodes following injection of nonself spleen cells into footpads as described above.

PVG or ACI rats (3 per group) were given a single intravenous injection of 2 mg of each of the four peptides or saline. On the day of treatment, or on days 1, 7, or 10 after treatment, the right footpads were injected with 5×10$^6$ syngeneic splenocytes while the left footpads were injected with 5×10$^6$ allogeneic Lew splenocytes. Seven days after the footpad injections, the draining lymph nodes were removed, a single cell suspension was prepared, and the cell number determined.

The ratio of the number of cells recovered from the side injected with allogeneic versus syngeneic cells was approximately 3:1 in rats treated with saline, the A2.75–84 peptide, or the RT1$^a$.75–84 peptide. A similar ratio was observed in lymph nodes obtained from rats treated with the B7.75–84 or B2702.75–84 peptide within 24 hours of footpad injection. However, the ratio fell to 1:1 in rats treated with the B7.75–84 peptide 7 or 10 days prior to footpad challenge. The ratio in rats treated with the B2702.75–84 peptide 7 or 10 days prior to footpad injection was approximately 2:1.

Thus, both B7.75–84 and B2702.75–84, but neither A2.75–84 nor another control peptide, were effective in inhibiting the response to allogenic challenge in vivo when previously injected into rats. B7.75–84 appeared somewhat more effective than B2702.75–84.

C. Effect of Intravenous Administration of the Peptide Plus a Short Course of CsA on Cardiac Allograft Survival Since the B7.75–84 and B2702.75–84 peptides blocked cellular immunity in vivo, we examined their effects on allograft survival in rats. ACI (RT1$^a$) recipients were given abdominal heterotopic heart allografts from Lew donors (Moeller et al. 1993, supra; Ono and Lindsey. 1969, supra). Graft function was monitored by daily abdominal palpation, and rejection was scored as complete when the palpable ventricular contractions ceased.

Grafts survived 9–12 days in control rats receiving no therapy. Allograft survival was similar (7–13 days) in recipients treated with 2–5 doses of B7.75–84 either in the two weeks before or in the 4 days following the transplant.

Therefore, we elected to combine peptide therapy with a subtherapeutic regimen of CsA. When CsA was administered as a single dose (20 mg/kg) two days after transplantation, 16 of 17 rats rejected their grafts by day 23. However, 4 of 7 rats that received 4 treatments with 10 mg of B7.75–84 in the two weeks before surgery and a single dose of CsA two days after surgery retained their grafts indefinitely (>200 days) (p=0.0023 compared to CsA alone). All rats treated with 20 mg of B7.75–84 on days −7 and −1 before transplantation and then with a single dose of CsA on day 2 after surgery rejected their grafts by day 16. This result indicates that the timing of peptide administration is critical since the total dose of B7.75–84 given was identical in the two groups.

An alternate treatment protocol in which the rats were given CsA (10 mg/kg) daily on days 0–4 after surgery was also evaluated. The majority of these grafts (14/17) were rejected by 30 days after transplantation. Fifty percent (4/8) of animals treated with 20 mg of B7.75–84 on days −7 and −1 prior to transplantation and then given CsA on days 0–4 retained their grafts for >200 days (p=0.0849 compared to CsA alone). This is in contrast to the finding that rats given the identical peptide regimen combined with a single dose of CsA on day 2 rejected their grafts by day 16. Treatment of animals with 10 mg of B7.75–84 on days −14, −12, −10, and −7 followed by CsA on days 04 after transplantation resulted in tolerance in 23/29 animals (80%) (p <0.0001 compared to CsA alone). Lastly, 7/11 rats treated concomitantly with B7.75–84 peptide and CsA on days 0–4 after transplantation retained their grafts for >200 days (p=0.0090 compared to CsA alone).

In summary, these results indicate that the B7.75–84 peptide could induce graft tolerance when used in combination with a subtherapeutic dose of CsA. Peptide treatment was effective when administered in the period before or after the transplant.

The synergistic effect of CsA and peptide on allograft survival was dependent on the peptide sequence: transplants in rats treated with the B2702.75–84 peptide in the two week period before transplantation or in the 4 days after surgery in combination with CsA on days 0–4 were rejected similarly to allografts in animals treated with CsA alone.

These results indicate that in the protocols tested above, B7.75–84 but not B2702.75–84 was helpful in preventing rejection of allografts in the foregoing rat protocols.

D. Demonstration of Donor Specificity of Tolerance

Although the majority of rats treated with the combination of B7.75–84 plus CsA did not reject their grafts, it remained possible that the animals were not tolerant. Treatment may have produced a general immunosuppressed state or the graft may have lost antigen presenting function or down-regulated MHC. To differentiate between tolerance and these other possibilities, rats that had retained their grafts for a minimum of 100 days were retransplanted with a second abdominal heart allograft distal to the primary graft. No further peptide or CsA treatments were given. Rats that received a second heart allograft from Brown Norway (BN) (RT1$^n$) donors (n=4) rejected the BN allograft by day 14 while those that received a second heart graft from the same strain as the original donor (n=3) accepted the second allograft indefinitely.

To assess the tissue specificity of this tolerance, animals that had maintained their heart grafts for >100 days were given two full-thickness abdominal skin allografts (n=4): the graft on the left side was from a BN donor and that on the right was from a Lew donor. Again, no additional peptide or CsA was administered. The BN skin grafts were rejected by day 11 while the Lew skin graft showed no signs of rejection (>200 days). Interestingly, rejection of a second allograft (heart or skin) did not affect the function of the original cardiac allograft.

Rats treated with the B7.75–84 peptide plus a subtherapeutic dose of CsA thus exhibit donor specific tolerance.

E. Effect of Oral Administration

The route by which a drug is given can often affect its potency. Carpenter and coworkers have reported that intrathymic injection of synthetic peptides corresponding to non-helical regions of rat MHC class II molecules prolonged the survival of vascularized allografts (Sayegh, et al. *Transplant Proc.* (1993) 25:357). In contrast, Fabre and colleagues found that synthetic peptides corresponding to residues 57–80 of the RT1A$^a$ molecule were immunogenic rather than tolerogenic when administered in complete Freund's adjuvant (Fangmann et al. *Transplant Proc.* (1993) 25:183). It was determined whether administration of the B7.75–84 peptide orally would induce tolerance to an allograft.

Rats treated orally with peptide alone rejected their grafts with normal kinetics. However, 8/12 animals given the peptide orally on days −14, −12, −10, and −7 prior to transplantation and 9/12 animals treated on days 0–4 after surgery in combination with CsA on days 0–4 maintained their grafts for >200 days (p=0.005 and 0.0007 respectively, compared with CsA alone). In addition, when the rats that had retained their cardiac allografts were given subsequent skin allografts from donor and third party, they rejected the third party grafts but not the donor skin grafts.

Thus, the immunomodulatory effects of the B7.75–84 peptide could be achieved by either oral or intravenous administration.

F. Mechanism of B7.75–84 Peptide-Induced Tolerance.

To investigate mechanisms by which the B7.75–84 peptide modified the response to alloantigens, several immunologic parameters were examined. Fluorescence activated cell sorter analysis showed that there were no differences in the absolute number of cells or percentage of CD4+ and CD8+ subsets in thymus or spleen isolated from peptide treated versus naive rats. Mitogen or alloantigen induced proliferation of spleen cells obtained from peptide treated rats was identical to that of controls. In addition, splenocytes from tolerant rats were unable to directly suppress an alloresponse in naive rats, indicating that "suppressor" cells were not involved. However, donor reactive cells could be demonstrated in tolerant rats. Using limiting dilution analysis, we found that the precursor frequency of Lew specific CTL in splenocytes obtained from naive ACI animals was 1 in 303,611. The frequency of Lew specific CTL precursors in splenocytes obtained from ACI rats that had maintained a Lewis heart allograft for more than 100 days was 1 in 98,646. These results suggest that anergic donor reactive cells were present in vivo and that these cells were released from anergy by exogenous cytokines that were added to the limiting dilution cultures in vitro (Jenkins and Miller *Faseb J.* (1992) 6:2428; Atteis etal. *J. Exp. Med.* (1991) 175:491). It should be noted that the only sequence available for a rat MHC Class I molecule is the RT1A molecule, which is identical with the B7.75–84 in seven of ten amino acids, in contrast to the B2702.75–84 peptide which is identical to the RT1A sequence in only five often residues (RT1A.75–84 RVDLRTLRGY SEQ ID NO:29)

G. Antibody Response

None of these peptides was able to modulate antibody responses in rats to the soluble protein antigen, keyhole limpet hemocyanin (KLH). Administration of peptides to rats prior to, concomitant with, or following immunization with KLH did not alter the titer of anti-KLH antibody that was detected in serum obtained 7 or 14 days later.

EXAMPLE 3

Effect of the Peptides on Allograft Rejection in Mice

According to the protocol in Example 3C, rats treated with B2702.75–84 peptide in combination with CsA did not show prevention of allograft rejection. Similar protocols conducted in mice show that the B2702.75–84 peptide is capable of conferring such tolerance.

Following the procedure set forth in Example 3C, daily administration of B2702.75–84 (80 mg/kg/day:ip) to CBA mice with (H-2$^k$) recipients of a C57B1/6 with (H-2$^b$) murine heart allograft prolonged graft survival to 11.4±2.6 days compared to 7.5±1.2 days in untreated control animals (n=8; p<0.01, Mann-Whitney U Test). The therapy using the same compound starting at day 5 after transplantation, prolonged graft survival to 9.2±0.4 days (n=5; p<0.02) indicating the subject composition could be useful in an ongoing rejection episode. In combination with a subtherapeutic dose of cyclosporin A (2.7 mg/kg/day; ip; day 0–4) the subject peptide prolonged graft survival to at least 45 days (3 grafts out of 4 still beating) compared to a median graft survival of 14 days in animals that received cyclosporin A monotherapy. Thus, B2702.75–84 is highly effective in mice.

When the B2702.75–84 was prepared as the D-isomer (all amino acids in the D-form) and administered to murine graft recipients at 10 mg/kg/day (ip; day 0–10), graft survival was prolonged to more than 22 days in 4 out of 5 animals (4 grafts out of 5 still beating). From these data, the D-isomer appears more potent than the L-isomer in vivo.

It is evident from these results, that substantial advantages ensue by substituting one or more of the amino acids with the unnatural D-amino acid to enhance physiological stability.

In an additional series of experiments, B2702.84–75/75–84 was tested in a murine model of Graft Versus Host Disease (GVHD). Donor/recipient mice were matched at their major histocompatibility complex loci, but mismatched at minor loci, a situation which closely approximates that of 90% of bone marrow transplant recipients. Recipient mice were lethally irradiated (900R) and given a combination of bone marrow and spleen cells from donor animals. In the absence of treatment with B2702.84–75/75–84, all animals showed evidence of GVHD in 30 days. However, mice that were treated with this peptide at 100 µg/mouse/ip daily for 35 days did not evidence GVHD at that time. In the following 20 days, some of these mice, however, developed GVHD. This outcome is expected to improve by combining administration of the peptide with subtherapeutic cyclosporin A.

The compounds of the invention can be used to greatly enhance the acceptance of transplants, either by themselves or in conjunction with other drugs, particularly immunosuppressant drugs. The ability to modulate activation of CTL provides many opportunities for inhibiting lysis in vitro and in vivo.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A peptide compound having immunomodulating activity comprising the sequence: RENLRIALRY (SEQ ID NO:12), wherein all of the amino acids are the D isomer and said immunomodulating activity is the inhibition of cytolysis by T cells in vitro and is greater than the immunomodulating activity of corresponding L-isoform peptides.

2. A pharmaceutical composition comprising the peptide compound of claim 1, and a subtherapeutic dosage of an immunosuppressant, together in an amount sufficient to inhibit transplant rejection in a mammal, in a physiologically acceptable medium.

3. A composition comprising the peptide compound of claim 1, and a subtherapeutic dosage of an immunosuprressant, together in an amount sufficient to inhibit transplant rejection in a mammal, in a physiologically acceptable medium.

* * * * *

UNITED STATES PATENT AND TRADEMARK OFFICE
CERTIFICATE OF CORRECTION

PATENT NO. : 6,436,903 B1
DATED : August 20, 2002
INVENTOR(S) : Carol A. Clayberger et al.

It is certified that error appears in the above-identified patent and that said Letters Patent is hereby corrected as shown below:

<u>Column 1,</u>
Line 4, after the title, please insert the following as the first paragraph:
-- Reference to Government Funding
 This invention was made with Government support under contract 5 R01 Al22039 awarded by the National Institutes of Health. The Government may have certain rights in this invention. --.

Signed and Sealed this

Sixth Day of September, 2005

JON W. DUDAS
*Director of the United States Patent and Trademark Office*

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 10 amino acids

```
              (B) TYPE: amino acid
              (C) STRANDEDNESS: single
              (D) TOPOLOGY: linear (ix) FEATURE:
              (A) NAME/KEY: Modified-site
              (B) LOCATION: 2
              (D) OTHER INFORMATION: /label= aa76
                  /note= "E or V"

(ix) FEATURE:
              (A) NAME/KEY: Modified-site
              (B) LOCATION: 3
              (D) OTHER INFORMATION: /label= aa77
                  /note= "D, S or N"

(ix) FEATURE:
              (A) NAME/KEY: Modified-site
              (B) LOCATION: 5
              (D) OTHER INFORMATION: /label= aa79
                  /note= "R or G"

(ix) FEATURE:
              (A) NAME/KEY: Modified-site
              (B) LOCATION: 6
              (D) OTHER INFORMATION: /label= aa80
                  /note= "I or N"

(ix) FEATURE:
              (A) NAME/KEY: Modified-site
              (B) LOCATION: 7
              (D) OTHER INFORMATION: /label= aa81
                  /note= "a small, hydrophobic amino acid"

(ix) FEATURE:
              (A) NAME/KEY: Modified-site
              (B) LOCATION: 8
              (D) OTHER INFORMATION: /label= aa82
                  /note= "R or L"

(ix) FEATURE:
              (A) NAME/KEY: Modified-site
              (B) LOCATION: 9
              (D) OTHER INFORMATION: /label= aa83
                  /note= "G or R"

(ix) FEATURE:
              (A) NAME/KEY: Modified-site
              (B) LOCATION: 10
              (D) OTHER INFORMATION: /label= aa84
                  /note= "a small or hydrophobic amino acid"

(ix) FEATURE:
              (A) NAME/KEY: Modified-site
              (B) LOCATION: 1..10
              (D) OTHER INFORMATION: /note= "at least one of the amino
                  acids is the D-isomer"

(xi) SEQUENCE DESCRIPTION: SEQ ID NO:1:

Arg Xaa Xaa Leu Xaa Xaa Xaa Xaa Xaa Xaa
 1               5                  10

(2) INFORMATION FOR SEQ ID NO:2:

(i) SEQUENCE CHARACTERISTICS:
              (A) LENGTH: 10 amino acids
              (B) TYPE: amino acid
              (C) STRANDEDNESS: single
              (D) TOPOLOGY: linear (ix) FEATURE:
              (A) NAME/KEY: Modified-site
              (B) LOCATION: 9
              (D) OTHER INFORMATION: /label= aa76
                  /note= "E or V"

(ix) FEATURE:
```

```
        (A) NAME/KEY: Modified-site
        (B) LOCATION: 8
        (D) OTHER INFORMATION: /label= aa77
            /note= "D, S or N"

(ix) FEATURE:
        (A) NAME/KEY: Modified-site
        (B) LOCATION: 6
        (D) OTHER INFORMATION: /label= aa79
            /note= "R or G"

(ix) FEATURE:
        (A) NAME/KEY: Modified-site
        (B) LOCATION: 5
        (D) OTHER INFORMATION: /label= aa80
            /note= "I or N"

(ix) FEATURE:
        (A) NAME/KEY: Modified-site
        (B) LOCATION: 4
        (D) OTHER INFORMATION: /label= aa81
            /note= "a small, hydrophobic amino acid"

(ix) FEATURE:
        (A) NAME/KEY: Modified-site
        (B) LOCATION: 3
        (D) OTHER INFORMATION: /label= aa82
            /note= "R or L"

(ix) FEATURE:
        (A) NAME/KEY: Modified-site
        (B) LOCATION: 2
        (D) OTHER INFORMATION: /label= aa83
            /note= "G or R"

(ix) FEATURE:
        (A) NAME/KEY: Modified-site
        (B) LOCATION: 1
        (D) OTHER INFORMATION: /label= aa84
            /note= "a small or hydrophobic amino acid"

(ix) FEATURE:
        (A) NAME/KEY: Modified-site
        (B) LOCATION: 1..10
        (D) OTHER INFORMATION: /note= "at least one of the amino
            acids is the D isomer"

(xi) SEQUENCE DESCRIPTION: SEQ ID NO:2:

Xaa Xaa Xaa Xaa Xaa Xaa Leu Xaa Xaa Arg
1               5                   10

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /label= X1
            /note= "any amino acid, polar or non-polar, preferably
            polar, either charged or uncharged"

(ix) FEATURE:
        (A) NAME/KEY: Modified-site
        (B) LOCATION: 6
        (D) OTHER INFORMATION: /label= X2
            /note= "preferably an amino acid of at least five carbon
            atoms, which may be polar or non-polar, particularly Asp
            and Ile"

(ix) FEATURE:
        (A) NAME/KEY: Modified-site
        (B) LOCATION: 7
```

(D) OTHER INFORMATION: /label= X3
                /note= "may be non-polar aliphatic from 2 to 6 carbon
                atoms(i.e., hydrophobic or small), more particularly 3 to
                5 carbon atoms, especially Ile"

(ix) FEATURE:
            (A) NAME/KEY: Modified-site
            (B) LOCATION: 8
            (D) OTHER INFORMATION: /label= X4
                /note= "any amino acid, particularly aliphatic, either
                charged or uncharged, preferably at least about five
                carbon atoms, such as Arg and Ile"

(ix) FEATURE:
            (A) NAME/KEY: Modified-site
            (B) LOCATION: 9
            (D) OTHER INFORMATION: /label= X5
                /note= "any amino acid, preferably aliphatic, charged or
                uncharged, polar or non-polar, particularly Gly and Arg,
                more particularly one of X4 and X5 is Arg"

(ix) FEATURE:
            (A) NAME/KEY: Modified-site
            (B) LOCATION: 10
            (D) OTHER INFORMATION: /label= X6
                /note= "any amino acid, preferably hydrophobic or small"

(ix) FEATURE:
            (A) NAME/KEY: Modified-site
            (B) LOCATION: group(3, 6..10)
            (D) OTHER INFORMATION: /note= "X1-X6 will be S,N,L,R,G,Y
                or N,I,A,L,R,Y or D,I,L,L,R,Y, respectively, where one of
                the amino acids in one group may be substituted at the
                same site for the amino acid in the other group."

(xi) SEQUENCE DESCRIPTION: SEQ ID NO:3:

Arg Glu Xaa Leu Arg Xaa Xaa Xaa Xaa Xaa
1               5                   10

(2) INFORMATION FOR SEQ ID NO:4:

(i) SEQUENCE CHARACTERISTICS:
            (A) LENGTH: 5 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "D-Arg"

(xi) SEQUENCE DESCRIPTION: SEQ ID NO:4:

Xaa Ile Ala Leu Tyr
1               5

(2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "D-Arg"

(ix) FEATURE:
            (A) NAME/KEY: Modified-site
            (B) LOCATION: 2
            (D) OTHER INFORMATION: /note= "D-Ile"

(ix) FEATURE:

```
            (A) NAME/KEY: Modified-site
            (B) LOCATION: 3
            (D) OTHER INFORMATION: /note= "D-Ala"

(ix) FEATURE:
            (A) NAME/KEY: Modified-site
            (B) LOCATION: 4
            (D) OTHER INFORMATION: /note= "D-Leu"

(ix) FEATURE:
            (A) NAME/KEY: Modified-site
            (B) LOCATION: 5
            (D) OTHER INFORMATION: /note= "D-Ser"

(xi) SEQUENCE DESCRIPTION: SEQ ID NO:5:

Xaa Xaa Xaa Xaa Xaa
1               5

(2) INFORMATION FOR SEQ ID NO:6:

(i) SEQUENCE CHARACTERISTICS:
            (A) LENGTH: 6 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 4
            (D) OTHER INFORMATION: /note= "D-Leu"

(xi) SEQUENCE DESCRIPTION: SEQ ID NO:6:

Arg Ile Leu Xaa Arg Tyr
1               5

(2) INFORMATION FOR SEQ ID NO:7:

(i) SEQUENCE CHARACTERISTICS:
            (A) LENGTH: 6 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION: /note= "D-Arg"

(ix) FEATURE:
            (A) NAME/KEY: Modified-site
            (B) LOCATION: 2
            (D) OTHER INFORMATION: /note= "D-Ile"

(ix) FEATURE:
            (A) NAME/KEY: Modified-site
            (B) LOCATION: 3
            (D) OTHER INFORMATION: /note= "D-Leu"

(ix) FEATURE:
            (A) NAME/KEY: Modified-site
            (B) LOCATION: 4
            (D) OTHER INFORMATION: /note= "D-Leu"

(ix) FEATURE:
            (A) NAME/KEY: Modified-site
            (B) LOCATION: 5
            (D) OTHER INFORMATION: /note= "D-Arg"

(ix) FEATURE:
            (A) NAME/KEY: Modified-site
            (B) LOCATION: 6
            (D) OTHER INFORMATION: /note= "D-Tyr"

(xi) SEQUENCE DESCRIPTION: SEQ ID NO:7:
```

```
    Xaa Xaa Xaa Xaa Xaa Xaa
    1               5
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /note= "D-Ile"

(xi) SEQUENCE DESCRIPTION: SEQ ID NO:8:

```
Ser Leu Ala Xaa Arg
1               5
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "D-Tyr"

(ix) FEATURE:
        (A) NAME/KEY: Modified-site
        (B) LOCATION: 2
        (D) OTHER INFORMATION: /note= "D-Leu"

(ix) FEATURE:
        (A) NAME/KEY: Modified-site
        (B) LOCATION: 3
        (D) OTHER INFORMATION: /note= "D-Ala"

(ix) FEATURE:
        (A) NAME/KEY: Modified-site
        (B) LOCATION: 4
        (D) OTHER INFORMATION: /note= "D-Ile"

(ix) FEATURE:
        (A) NAME/KEY: Modified-site
        (B) LOCATION: 5
        (D) OTHER INFORMATION: /note= "D-Arg"

(xi) SEQUENCE DESCRIPTION: SEQ ID NO:9:

```
Xaa Xaa Xaa Xaa Xaa
1               5
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /note= "D-Leu"

(xi) SEQUENCE DESCRIPTION: SEQ ID NO:10:

```
Ser Arg Leu Xaa Ile Arg
1               5
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "D-Tyr"

(ix) FEATURE:
        (A) NAME/KEY: Modified-site
        (B) LOCATION: 2
        (D) OTHER INFORMATION: /note= "D-Arg"

(ix) FEATURE:
        (A) NAME/KEY: Modified-site
        (B) LOCATION: 3
        (D) OTHER INFORMATION: /note= "D-Leu"

(ix) FEATURE:
        (A) NAME/KEY: Modified-site
        (B) LOCATION: 4
        (D) OTHER INFORMATION: /note= "D-Leu"

(ix) FEATURE:
        (A) NAME/KEY: Modified-site
        (B) LOCATION: 5
        (D) OTHER INFORMATION: /note= "D-Ile"

(ix) FEATURE:
        (A) NAME/KEY: Modified-site
        (B) LOCATION: 6
        (D) OTHER INFORMATION: /note= "D-Arg"

(xi) SEQUENCE DESCRIPTION: SEQ ID NO:11:

```
Xaa Xaa Xaa Xaa Xaa Xaa
1               5
```

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2702.75-84

(xi) SEQUENCE DESCRIPTION: SEQ ID NO:12:

```
Arg Glu Asn Leu Arg Ile Ala Leu Arg Tyr
1               5                   10
```

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2705.75-84

(xi) SEQUENCE DESCRIPTION: SEQ ID NO:13:

```
Arg Glu Asp Leu Arg Thr Leu Leu Arg Tyr
1               5                   10

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B7.75-84

(ix) FEATURE:
        (A) NAME/KEY: Peptide
        (B) LOCATION: 1..10
        (D) OTHER INFORMATION: /note= "B7.75-84"

(xi) SEQUENCE DESCRIPTION: SEQ ID NO:14:

Arg Glu Ser Leu Arg Asn Leu Arg Gly Tyr
1               5                   10

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2702.75-84D^77

(ix) FEATURE:
        (A) NAME/KEY: Peptide
        (B) LOCATION: 1..10
        (D) OTHER INFORMATION: /note= "B2702.75-84D^77"

(xi) SEQUENCE DESCRIPTION: SEQ ID NO:15:

Arg Glu Asp Leu Arg Ile Ala Leu Arg Tyr
1               5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2702.75-84T^80

(xi) SEQUENCE DESCRIPTION: SEQ ID NO:16:

Arg Glu Asn Leu Arg Thr Ala Leu Arg Tyr
1               5                   10

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear
```

```
    (ii) MOLECULE TYPE: peptide (vi) ORIGINAL SOURCE:
         (C) INDIVIDUAL ISOLATE: B2702.75-84L^81

(xi) SEQUENCE DESCRIPTION: SEQ ID NO:17:

Arg Glu Asn Leu Arg Ile Leu Leu Arg Tyr
1               5                   10

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (vi) ORIGINAL SOURCE:
         (C) INDIVIDUAL ISOLATE: B2702.84-75/75-84

(xi) SEQUENCE DESCRIPTION: SEQ ID NO:18:

Tyr Arg Leu Ala Ile Arg Leu Asn Glu Arg Arg Glu Asn Leu Arg Ile
1               5                   10                  15

Ala Leu Arg Tyr
            20

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (vi) ORIGINAL SOURCE:
         (C) INDIVIDUAL ISOLATE: B7.84-75/75-84

(xi) SEQUENCE DESCRIPTION: SEQ ID NO:19:

Tyr Gly Arg Leu Asn Arg Leu Ser Glu Arg Arg Glu Ser Leu Arg Asn
1               5                   10                  15

Leu Arg Gly Tyr
            20

(2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (vi) ORIGINAL SOURCE:
         (C) INDIVIDUAL ISOLATE: B2702.84-75T/75-84

(xi) SEQUENCE DESCRIPTION: SEQ ID NO:20:

Tyr Arg Leu Ala Thr Arg Leu Asn Glu Arg Arg Glu Asn Leu Arg Ile
1               5                   10                  15

Ala Leu Arg Tyr
            20

(2) INFORMATION FOR SEQ ID NO:21:
```

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (vi) ORIGINAL SOURCE:
    (C) INDIVIDUAL ISOLATE: B7202.84-75/75-84T (xi) SEQUENCE DESCRIPTION: SEQ ID NO:21:

Tyr Arg Leu Ala Ile Arg Leu Asn Glu Arg Arg Glu Asn Leu Arg Thr
1               5                   10                  15

Ala Leu Arg Tyr
            20

(2) INFORMATION FOR SEQ ID NO:22:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B7202.84-75T/75-84T (xi) SEQUENCE DESCRIPTION: SEQ ID NO:22:

Tyr Arg Leu Ala Thr Arg Leu Asn Glu Arg Arg Glu Asn Leu Arg Thr
1               5                   10                  15

Ala Leu Arg Tyr
            20

(2) INFORMATION FOR SEQ ID NO:23:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2702.84-75/84-75

(xi) SEQUENCE DESCRIPTION: SEQ ID NO:23:

Tyr Arg Leu Ala Ile Arg Leu Asn Glu Arg Tyr Arg Leu Ala Ile Arg
1               5                   10                  15

Leu Asn Glu Arg
            20

(2) INFORMATION FOR SEQ ID NO:24:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2702.60-84

(xi) SEQUENCE DESCRIPTION: SEQ ID NO:24:

```
Trp Asp Arg Glu Thr Gln Ile Cys Lys Ala Lys Ala Gln Thr Asp Arg
1               5                   10                  15

Glu Asn Leu Arg Ile Ala Leu Arg Tyr
            20              25
```

(2) INFORMATION FOR SEQ ID NO:25:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B2702.70-84

(xi) SEQUENCE DESCRIPTION: SEQ ID NO:25:

```
Lys Ala Gln Thr Asp Arg Glu Asn Leu Arg Ile Ala Leu Arg Tyr
1               5                   10                  15
```

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B7.75-84

(xi) SEQUENCE DESCRIPTION: SEQ ID NO:26:

```
Arg Glu Ser Leu Arg Asn Leu Arg Gly Tyr
1               5                   10
```

(2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: B7.84-75/75-84

(xi) SEQUENCE DESCRIPTION: SEQ ID NO:27:

```
Gln Gly Arg Leu Asn Lys Ala Ser Thr Asp Arg Glu Ser Leu Arg Asn
1               5                   10                  15

Leu Arg Gly Tyr
            20
```

(2) INFORMATION FOR SEQ ID NO:28:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:

(C) INDIVIDUAL ISOLATE: B2702.84-79/79-84

(xi) SEQUENCE DESCRIPTION: SEQ ID NO:28:

Tyr Arg Leu Ala Ile Arg Arg Ile Ala Leu Arg Tyr
1               5                   10

(2) INFORMATION FOR SEQ ID NO:29:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: RT1A.75-84

(xi) SEQUENCE DESCRIPTION: SEQ ID NO:29:

Arg Val Asp Leu Arg Thr Leu Arg Gly Tyr
1               5                   10

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:30:

Arg Ile Ala Leu Arg Tyr
1               5

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:31:

Arg Ile Leu Leu Arg Tyr
1               5

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:32:

Tyr Arg Leu Ala Ile Arg
1               5

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:33:

Tyr Arg Leu Leu Ile Arg
1               5

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:34:

Tyr Arg Leu Ala Ile Arg Leu Asn Glu Arg
1               5                   10

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:35:

Tyr Arg Leu Leu Ile Arg Leu Asn Glu Arg
1               5                   10

(2) INFORMATION FOR SEQ ID NO:36:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:36:

Tyr Arg Leu Ala Ile Arg Leu Asp Glu Arg
1               5                   10

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:37:

Arg Glu Asp Leu Arg Ile Leu Leu Arg Tyr
1               5                   10

(2) INFORMATION FOR SEQ ID NO:38:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:38:

Tyr Arg Leu Leu Ile Arg Leu Asp Glu Arg
1               5                   10